(12) United States Patent
Paris et al.

(10) Patent No.: US 11,806,053 B2
(45) Date of Patent: Nov. 7, 2023

(54) POLYMERIC VERTEBRAL RETAINING DEVICES

(71) Applicant: Orthofix US LLC, Lewisville, TX (US)

(72) Inventors: Alain Paris, Pontarlier (FR); Lukas Glutz, Ins (CH); David Chenaux, Corcelles (CH); Nick Koske, Lewisville, TX (US)

(73) Assignee: Orthofix US LLC, Lewisville, TX (US)

( * ) Notice: Subject to any disclaimer, the term of this patent is extended or adjusted under 35 U.S.C. 154(b) by 0 days.

(21) Appl. No.: 17/682,920

(22) Filed: Feb. 28, 2022

(65) Prior Publication Data

US 2023/0270477 A1  Aug. 31, 2023

(51) Int. Cl.
*A61B 17/70* (2006.01)
*A61B 17/68* (2006.01)

(52) U.S. Cl.
CPC ...... *A61B 17/7091* (2013.01); *A61B 17/7076* (2013.01); *A61B 2017/681* (2013.01)

(58) Field of Classification Search
CPC .......... A61B 2017/0256; A61B 17/025; A61B 17/7076; A61B 17/7077; A61B 17/70; A61B 17/02; A61B 2017/681
USPC ...... 606/205, 86 A, 246, 105; 600/200, 218, 600/219, 222, 226
See application file for complete search history.

(56) References Cited

U.S. PATENT DOCUMENTS

| | | | |
|---|---|---|---|
| 2014/0012269 A1* | 1/2014 | Bass | A61B 17/025 606/90 |
| 2014/0031828 A1* | 1/2014 | Patel | A61B 17/7077 606/90 |
| 2014/0249591 A1* | 9/2014 | Peultier | A61B 17/7077 606/86 A |
| 2014/0257035 A1* | 9/2014 | Blain | A61B 5/389 600/104 |
| 2017/0042524 A1* | 2/2017 | Angus | A61B 17/0218 |
| 2018/0249992 A1* | 9/2018 | Truckey | A61B 17/025 |
| 2021/0059656 A1* | 3/2021 | Otto | A61B 34/10 |
| 2021/0085370 A1* | 3/2021 | Klausman | A61B 17/708 |

* cited by examiner

*Primary Examiner* — Eduardo C Robert
*Assistant Examiner* — David C Comstock
(74) *Attorney, Agent, or Firm* — HAYNES AND BOONE, LLP

(57) ABSTRACT

Vertebral retaining devices and instruments are provided. A retaining device may include a first monolithic body having a first handle and first jaw pivotably coupled to a second monolithic body having a second handle and a second jaw. The first body and the second body may be pivotably coupled to one another at an intermediate region between the respective handles and jaws. In some aspects, the first and second bodies may be polymeric. The first jaw and second jaw may be shaped to provide an access region between the first jaw and the second jaw when the retaining device is coupled to bone fasteners attached to the vertebrae. The retaining device may include a locking assembly coupled to the first handle and the second handle, and configured to retain the first jaw and the second jaw in a spaced relationship relative to one another.

18 Claims, 15 Drawing Sheets

POLYMERIC VERTEBRAL RETAINING DEVICES

CROSS-REFERENCE TO RELATED APPLICATIONS

This application is related to U.S. Design patent application Ser. No. 29/828,733, filed Feb. 28, 2022, titled VERTEBRAL RETAINER, the entire disclosure of which is hereby incorporated herein by reference.

TECHNICAL FIELD

This disclosure is generally directed to devices for retaining vertebral bodies during spinal surgeries. For instance, a retaining device may include receiving portions to receive protruding portions of spinal fasteners inserted into the vertebrae, and one or more expansion mechanisms to distract and retain the vertebrae in a desired relationship.

BACKGROUND

The spinal column generally includes thirty three vertebrae extending from a cervical region of the spine to a lumbar region of the spine. The vertebrae are connected to one another by flexible fibrocartilaginous joints called intervertebral disks. Intervertebral discs include a gel-like nucleus surrounded by a fibrous structure called the anulus. Intervertebral discs, similar to other joints, can provide impact protection and flexibility to allow the spinal column to bend or flex while reducing friction between the vertebral bodies. Over time, the structure of the intervertebral discs may begin to degrade or suffer damage. In some instances, an impact or other injury-inducing event may cause a herniation of an intervertebral disc. With a herniation, a portion of the gel-like nucleus may bulge out from a tear in the annulus. Herniated or bulging discs may reduce the effectiveness of the disk at absorbing impact and reducing friction between the vertebrae. Further, a herniated disc can cause a portion of the bulging nucleus to pinch the nerves running along or from the spine. Pinched nerves in the spine can result in pain, numbness, or other undesirable symptoms.

Present interventions for addressing or correcting herniated discs include disc repair, spinal fusion, and prosthetic disc surgeries. Disc repair surgeries, which may include diskectomies, may involve removing the herniated portion of the disc, and repairing the annulus structure to prevent the nucleus material from bulging out of the herniation. In some instances, a diskectomy maybe insufficient or impractical. For example, if the herniation or degradation of the intervertebral disc is too severe, a surgeon may fuse together the two vertebrae on either side of the degraded disk to stabilize the spine. A fusion surgery may include, for example, removing the remainder of the intervertebral disc from the intervertebral space, inserting an intervertebral spacer between the vertebrae, and filling the remaining space between the vertebrae with bone graft material, which will solidify and attach to the vertebral bodies over time. Spinal fixation surgeries may further include driving bone screws with tulip-shaped heads into the vertebrae surrounding the degraded disc, and connecting the tulip-shaped heads to one another by connecting rods.

Recently, prosthetic intervertebral discs have been used by physicians to treat intervertebral disk injuries by imitating the function of an intervertebral disc. A prosthetic intervertebral disc may include a flexible or elastomeric nucleus between upper and lower plates. The upper and lower plates may be fixed to the respective vertebrae, with the elastomeric core between the plates. To implant the prosthetic disc, the surgeon first makes an incision in the patient's skin and surrounding tissues to provide access to the intervertebral space. The surgeon may use tissue-retracting instruments to maintain access through the incision to the intervertebral space. The surgeon may then remove or resect the disc from the intervertebral space, and prepare the surfaces of the vertebrae to receive and/or bond to the plates of the prosthetic intervertebral disc.

As the surgeon removes the existing disc material and prepares the surfaces of the vertebrae to receive the prosthetic disc, it may be helpful to retain the vertebrae in a fixed spaced relationship relative to one another. For example, the surgeon may drive one or more screws, pins, or other fasteners into the upper and lower vertebrae on either side of the disk space such that a proximal portion of the fasteners protrude away from the vertebrae and through the access channel in the tissue. The surgeon may engage the proximal protruding portions of the fasteners with the retaining tool, and control or adjust the distraction or compression of the vertebrae using the retaining tool. The instruments used for such surgeries may be constructed of expensive, high-quality stainless steel, titanium, or other metallic materials with high strength. The instruments may be kept and maintained by a surgical center or health care provider and used in multiple surgeries over a period of time. In some cases, storing and sterilizing the tools for future use can be burdensome for health practitioners.

SUMMARY

The present disclosure describes polymer-based retaining devices and instruments for retaining vertebrae in a spaced relationship during a spinal surgery. For example, a retaining device may include a first monolithic body having a first handle and first jaw coupled to a second monolithic body having a second handle and a second jaw. The first monolithic body and the second monolithic body may be pivotably coupled to one another at an intermediate region between the respective handles and jaws. In some aspects, the first and second monolithic bodies may be formed of a polymer by injection molding, 3D printing, and slash or any other suitable manufacturing technique. The first jaw and second jaw may be shaped and structurally arranged to provide an access region between the first jaw and the second jaw when the retaining device is coupled to bone fasteners attached to the vertebrae. In another aspect, the retaining device may include a locking assembly coupled to the first handle and the second handle. The locking assembly may be configured to retain the first jaw and the second jaw in a spaced relationship relative to one another. Accordingly, the locking assembly may be configured to maintain the connected vertebrae in a space relationship relative to one another. The structural design and configuration of the retaining devices described herein may allow for more simplified and less expensive manufacturing processes to be used, such as injection molding and 3D printing. Accordingly, the retaining devices described herein may be more suitable for single use or disposable use. Further, the structural design and components of the retaining devices described herein may provide for manufacturing using polymers or plastics while maintaining sufficient strength and rigidity so that the retaining device can be used in spinal surgeries.

According to one aspect of the present disclosure, an apparatus for retaining spinal vertebrae in a distracted state includes: a monolithic first body comprising: a first handle; a first jaw extending distally of the first handle; and a first canulated pin receiving member extending transverse to a longitudinal axis of the first body; a monolithic second body pivotably coupled to the first body at an intermediate portion of the first body between the first handle and the first jaw, the second body comprising: a second handle; a second jaw extending distally of the second handle; and a second canulated pin receiving member extending transverse to a longitudinal axis of the second body; and a locking assembly coupled to the first handle and the second handle, wherein the locking assembly is configured to selectively retain the first cannulated pin receiving member and the second cannulated pin receiving member at a plurality of relative spacings.

In some aspects, the first jaw comprises an arcuate shape, the second jaw comprises an arcuate shape, and a distal end of the second jaw extends toward a distal end of the first jaw. In some aspects, the second body further comprises a first projection at the intermediate portion, wherein the first projection extends transverse to the longitudinal axis of the first body and defines a first hinge pin aperture, the second body further comprises a second projection at an intermediate portion of the second body, where the first projection extends transverse to the longitudinal axis of the second body and defines a second hinge pin aperture, the apparatus further comprises a hinge pin positioned through the first hinge pin aperture and the second hinge pin aperture to retain the first body and second body in a pivotable engagement. In some aspects, the first canulated pin receiving member comprises a tubular body extending from a distal end of the first handle, wherein the second canulated pin receiving member comprises a tubular body extending from a distal end of the second handle.

In some aspects, the first canulated pin receiving member comprises a first flat surface on an inward-facing side of the first canulated pin receiving member, the second canulated pin receiving member comprises a second flat surface on an inward-facing side of the second canulated pin receiving member, and the first flat surface is configured to contact the second flat surface when the apparatus is in a closed position. In some aspects, the first body comprises a polymer material, and the second body comprises the polymer material. In some aspects, the first body comprises a first rib structure in at least one of the first handle or the first jaw, and the second body comprises a second rib structure in at least one of the second handle or the second jaw. In some aspects, the first body further comprises at least one solid exterior surface over at least one side of the first rib structure, and the second body further comprises at least one solid exterior surface over at least one side of the second rib structure.

In some aspects, the locking assembly comprises: a rack pivotably coupled to the first handle and the second handle, the rack comprising a first plurality of teeth; a pinion rotatably coupled to the first handle, the pinion comprising a second plurality of teeth configured to engage the first plurality of teeth; and a locking switch configured to lock the locking assembly at each of a plurality of positions corresponding to the plurality of relative spacings. In some aspects, the first handle defines a first slot configured to receive a first end of the rack, and wherein the second handle defines a second slot configured to receive a second end of the rack. In some aspects, the first end of the rack is configured to rotate within the first slot, and wherein the second end of the rack is configured to rotate within the second slot. In some aspects, the rack further comprises a third set of teeth, wherein the locking switch further comprises a fourth set of teeth, wherein the locking assembly further comprises a spring configured to bias the locking switch to engage the fourth set of teeth with the third set of teeth. In some aspects, the locking switch and the rack are configured to allow for ratcheting movement of the rack in a first direction and to inhibit movement of the rack in an opposite second direction.

In some aspects, the apparatus further includes a first pin engaging member coupled to the first pin receiving member and a second pin engaging member coupled to the second pin receiving member, where the first pin engaging member comprises a first locking tab configured to engage a retaining groove on a first pin, and the second pin engaging member comprises a second locking tab configured to engage a retaining groove on a second pin. In some aspects, the first pin engaging member is monolithic and comprises a flexible polymer, and wherein the second pin engaging member is monolithic and comprises a polymer. In some aspects, the first jaw comprises a first transition region defining a curve projecting toward a pin-receiving end of the first canulated pin receiving member, and wherein the second jaw comprises a second transition region defining a curve projecting toward a pin-receiving end of the second canulated pin receiving member. In some aspects, at least one of the first handle or the second handle comprises an I-beam structure.

According to another embodiment of the present disclosure, a vertebral retainer includes: a monolithic first body comprising: a first handle; a first jaw extending distally of the first handle; and a first pin receiving member configured to retain a first pin; a monolithic second body pivotably coupled to the first body at an intermediate portion of the first body between the first handle and the first jaw, the second body comprising: a second handle; a second jaw extending distally of the second handle; and a second pin receiving member configured to retain a second pin, wherein the monolithic first body comprises a rib structure in at least one of the first jaw or the first handle, the rib structure defining a plurality of intersecting ribs and a plurality of voids, and wherein the monolithic second body comprises a rib structure in at least one of the second jaw or the second handle, the rib structure defining a plurality of intersecting ribs and a plurality of voids.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following. One or more features of any embodiment or aspect may be combinable with one or more features of other embodiment or aspect.

BRIEF DESCRIPTION OF THE DRAWINGS

The accompanying drawings illustrate implementations of the systems, devices, and methods disclosed herein and together with the description, serve to explain the principles of the present disclosure.

Figure 1:
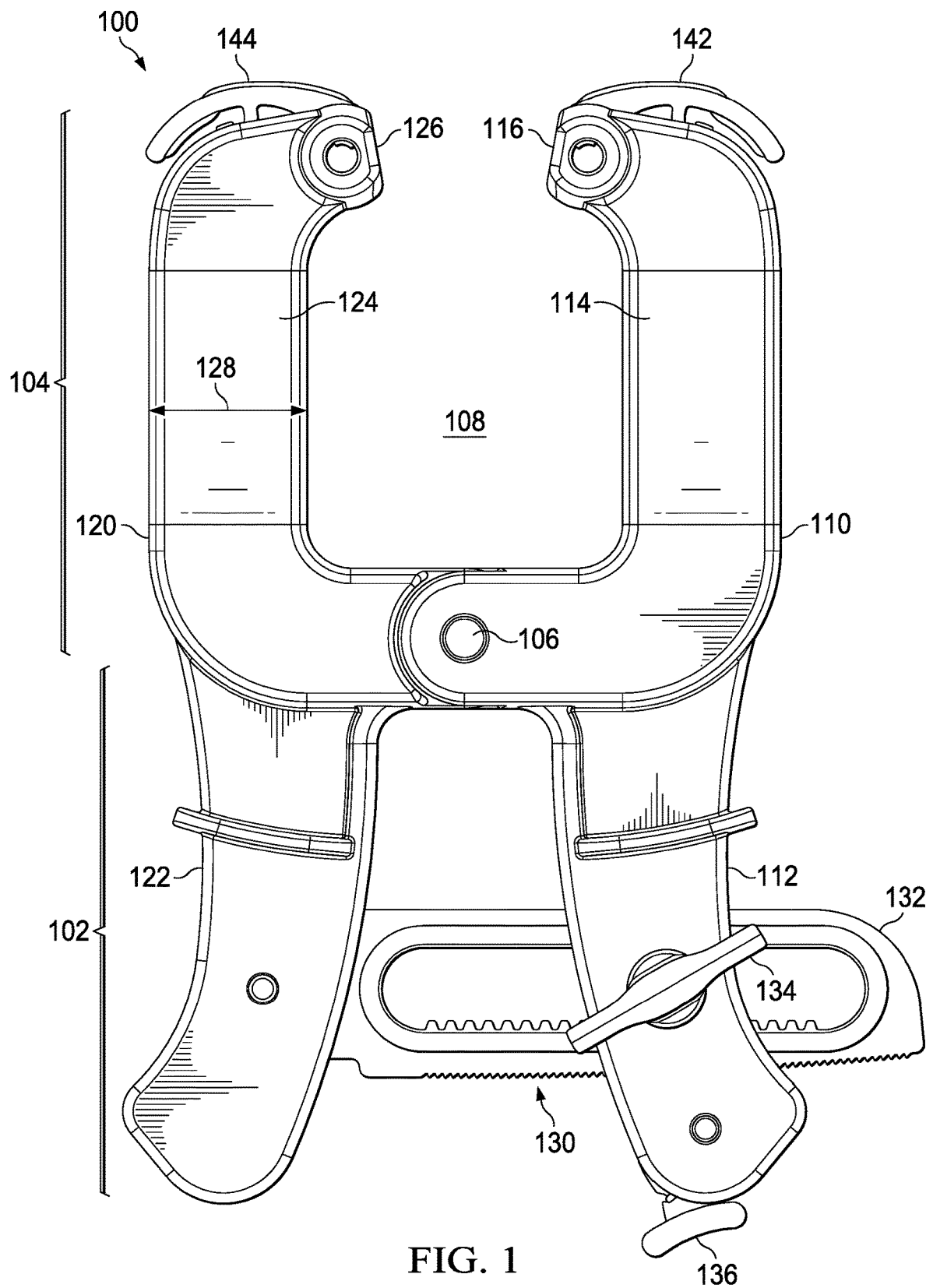
FIG. 1 is a top elevation view of a polymeric vertebral retraining device in accordance with an embodiment of the present disclosure.

These figures will be better understood by reference to the following Detailed Description.

DETAILED DESCRIPTION

For the purpose of promoting an understanding of the principles of the present disclosure, reference will now be made to the implementations illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In addition, this disclosure describes some elements or features in detail with respect to one or more implementations or figures, when those same elements or features appear in subsequent figures, without such a high level of detail. It is fully contemplated that the features, components, and/or steps described with respect to one or more implementations or figures may be combined with the features, components, and/or steps described with respect to other implementations or figures of the present disclosure. For simplicity, in some instances the same or similar reference numbers are used throughout the drawings to refer to the same or like parts.

FIGS. 1-8 provide various views of a vertebral retaining device 100, according to embodiments of the present disclosure. The vertebral retaining device 100 may be used in spinal surgeries, such as spinal fixation or prosthetic disc implantation. For example, referring to FIGS. 1 and 2, the vertebral retaining device 100 may be configured to engage and couple to bone fasteners protruding from vertebral bodies on either side of an intervertebral space. The retaining device 100 may be configured, in some aspects, to distract and retain the vertebral bodies at a desired spaced relationship. In the illustrated embodiment, the device 100 may be formed of a polymer or plastic material. However, one or more components of the device 100 may include metals such as stainless steel, aluminum, and/or titanium. The vertebral retaining device 100 includes a first body 110 coupled to a second body 120 by a hinge 106. The device 100 further includes a locking assembly 130 coupled to respective handles 112, 122 of the first and second bodies 110, 120. The device 100 further includes pin engaging members 142, 144 coupled to the first and second bodies 110, 120, and configured to provide for releasable engagement or connection with pins extending from the vertebrae. Each of the first body 110 and the second body 120 may be a monolithic structure. For the purposes of the present disclosure, "monolithic" may refer to a singular, unitary component which is formed by molding, casting, printing, or sintering, for example. In an exemplary embodiment, the first body 110 and the second body 120 are formed of a polymer by injection molding.

The device 100 includes a handle region 102 and a jaw region 104. A user may control the relative spacing of the pin receiving members 116, 126 of the jaw region 104 by actuating the handle region 102. The handles 112, 114 are pivotably coupled such that the handles 112, 114 are configured to pivot relative to each other about a pivoting axis. For example, by squeezing the handles 112, 122 together, the user may open the jaw region 104 to move the pin receiving members 116, 126 away from one another. Accordingly, by squeezing the handles 112, 122, the user may distract or separate the vertebrae via the pins disposed within the pin receiving members 116, 126. In some aspects, the curved profile of the handles 112, 114 may improve or increase the leverage provided by the physician in distracting the vertebrae. On the other hand, by expanding or relaxing the handles 112, 122 relative to one another, the user may draw the pin receiving members 116, 126 toward one another.

In some aspects, the user may provide more controlled or precise movement by using the locking assembly 130. The locking assembly 130 includes a thumbscrew-style actuator 134 to control the expansion of the handles 112, 122. The thumbscrew actuator 134 may include a pinion gear configured to engage a corresponding rack 132, where the rack 132 is coupled to the second handle 122 at a first end. Accordingly, by rotating the thumbscrew actuator 134, the distance between the handles 112, 122 can change. The locking assembly 130 may further include a ratchet member 136 configured to engage ratchet teeth on a bottom side of the rack 132. The ratchet member 136 and the ratchet teeth on the rack 132 may be configured to allow indexed movement in one direction, but not in the other direction. For example, the ratchet member 136 and the rack 132 may be configured to allow the handles 112, 122 to move toward one another, but may prevent or inhibit movement of the handles 112, 122 away from one another. In other words, the ratchet member 136 and the rack 132 may be configured to allow the pin receiving members 116, 126 of the jaw region 104 to move away from one another, but restrict movement of the pin receiving members 116, 126 toward one another. In the illustrated embodiment, the ratchet member 136 may have an unlocked configuration or position and a locked configuration or position. For example, by actuating the ratchet member 136 upward and toward the second handle 122, The ratchet member 136 may disengage the teeth on the bottom of the rack 132 to allow for free movement of the handles 112, 122 toward or away from one another.

In addition to the handles 112, 122, the first body 110 includes a first jaw member 114, and the second body 120 includes a second jaw member 124. The jaw members 114, 124 are shaped such that the distal ends of the jaw members near the pin receiving members 116, 126, curve inward toward one another. Accordingly, the jaw members 114, 124 form and interior space 108, which may provide the surgeon greater access to the surgical site. Further, in some aspects, the curved profile of the jaw members 114, 124 may provide for a more desirable movement profile between the pin receiving members 116, 126. In some aspects, the shapes of the jaw members 114, 124 may be described as D-shaped, or C-shaped. The first and second bodies 110, 120 include one or more widths at the handle region 102 and the jaw region 104. For example, the second jaw member 124 is shown having a width 128 in an intermediate region of the jaw member 124. In some aspects, the width 128 may provide sufficient strength and rigidity to support the forces involved with keeping the spinal vertebrae in a separated or distracted state. In particular, the width 128 may be sufficient such that a polymer or plastic material can be used for the bodies 110, 120. For example, in some aspects, the width 128 may range between 10 mm and 20 mm. For example, the width 128 may be approximately 13 mm, 14 mm, 15 mm, 16 mm, 17 mm, and/or any other suitable width, both greater or smaller. Further, as explained below, the jaw members 114, 124 may have a depth or thickness ranging between 15 mm and 30 mm, including values such as 15 mm, 18 mm, 19 mm, 20 mm, 22 mm, and/or any other suitable value, both greater or smaller. In some aspects, the jaw members 114, 124 may have cross-sectional areas ranging between 200 mm$^2$ and 400 mm$^2$, where the cross-sectional area is determined based on the outermost exterior surfaces of the jaw members 114, 124 and taken along a plane transverse to the longitudinal axis of the device 100. The lengths of the jaw region 104 may range from approximately 50 mm to approximately 85 mm.

Figure 3:
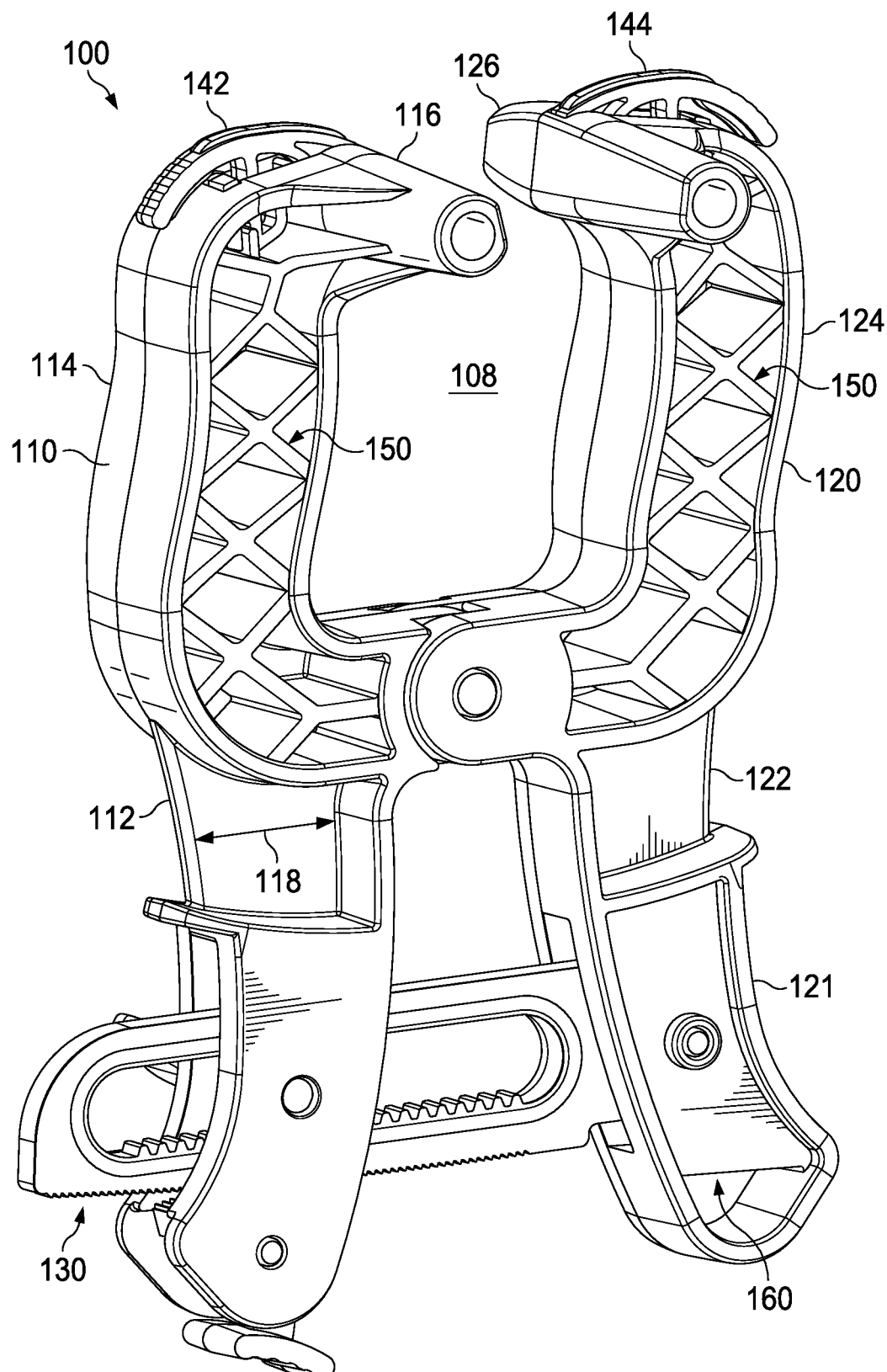
FIG. 3 is a perspective view of a rear side of the polymeric vertebral retraining device of FIG. 1 in accordance with an embodiment of the present disclosure.
Figure 4:
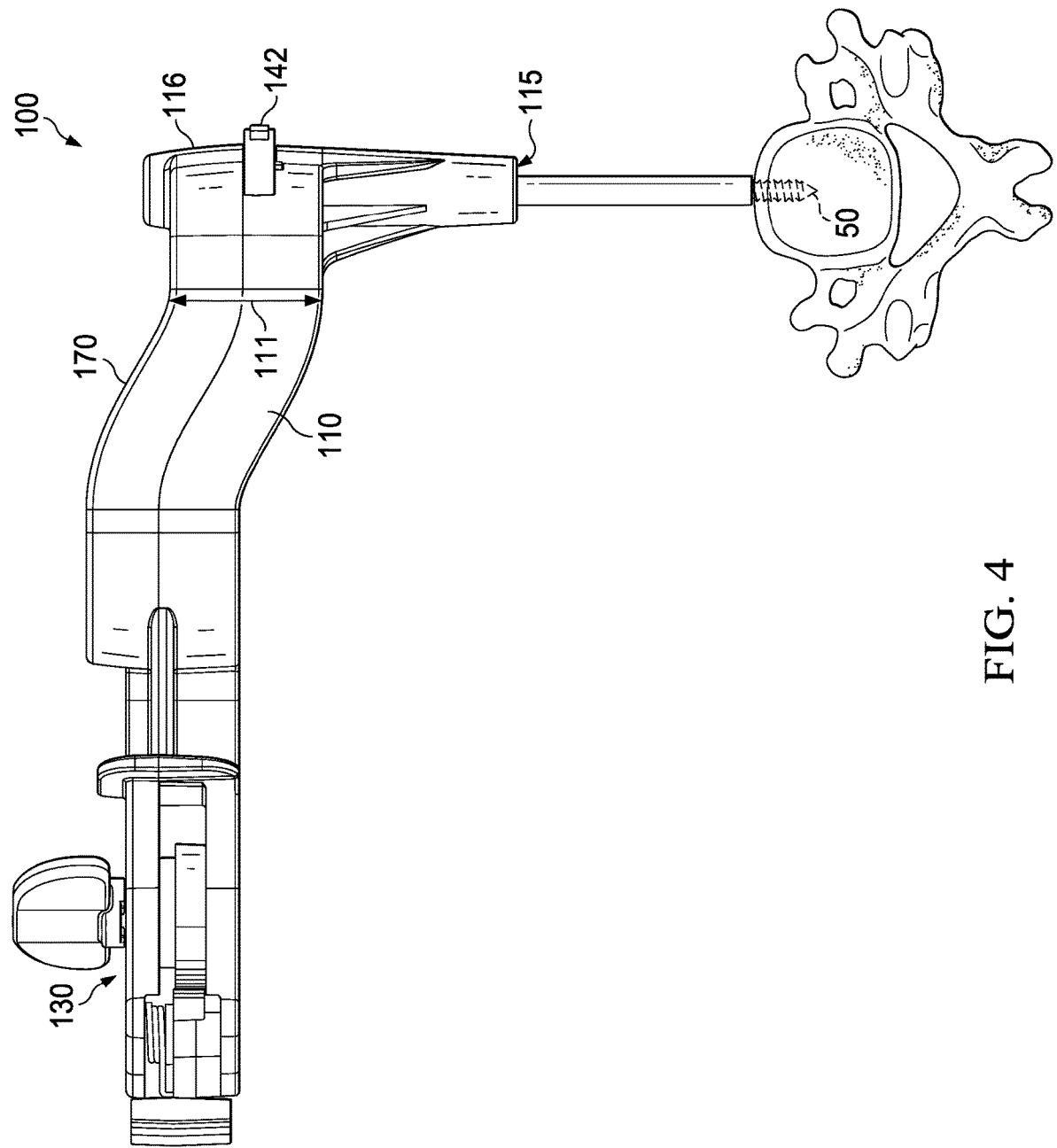
FIG. 4 is an elevation view of a lateral side of the polymeric vertebral retraining device of FIG. 1 in accordance with an embodiment of the present disclosure.

The pin receiving members 116, 126 include downwardly-extending tubular bodies having inner diameters configured to receive protruding portions of bone screws or pins attached to the vertebrae (see FIG. 4). The pin engaging members 142, 144 are coupled to the first jaw member 114 and second jaw member 124, respectively, via corresponding cavities in the distal region of the jaw members 114, 124. The cavities in which the pin engaging members 142, 144 are positioned are in communication with the cannulas or passages in the pin receiving members 116, 126. As will be explained further below, the pin engaging members 142, 144 of the embodiment of FIGS. 1-8 each include locking tabs extending into the passages of the pin receiving members 116, 126. The locking tabs may be configured to engage corresponding grooves in the pins protruding from the vertebrae.

Figure 2:
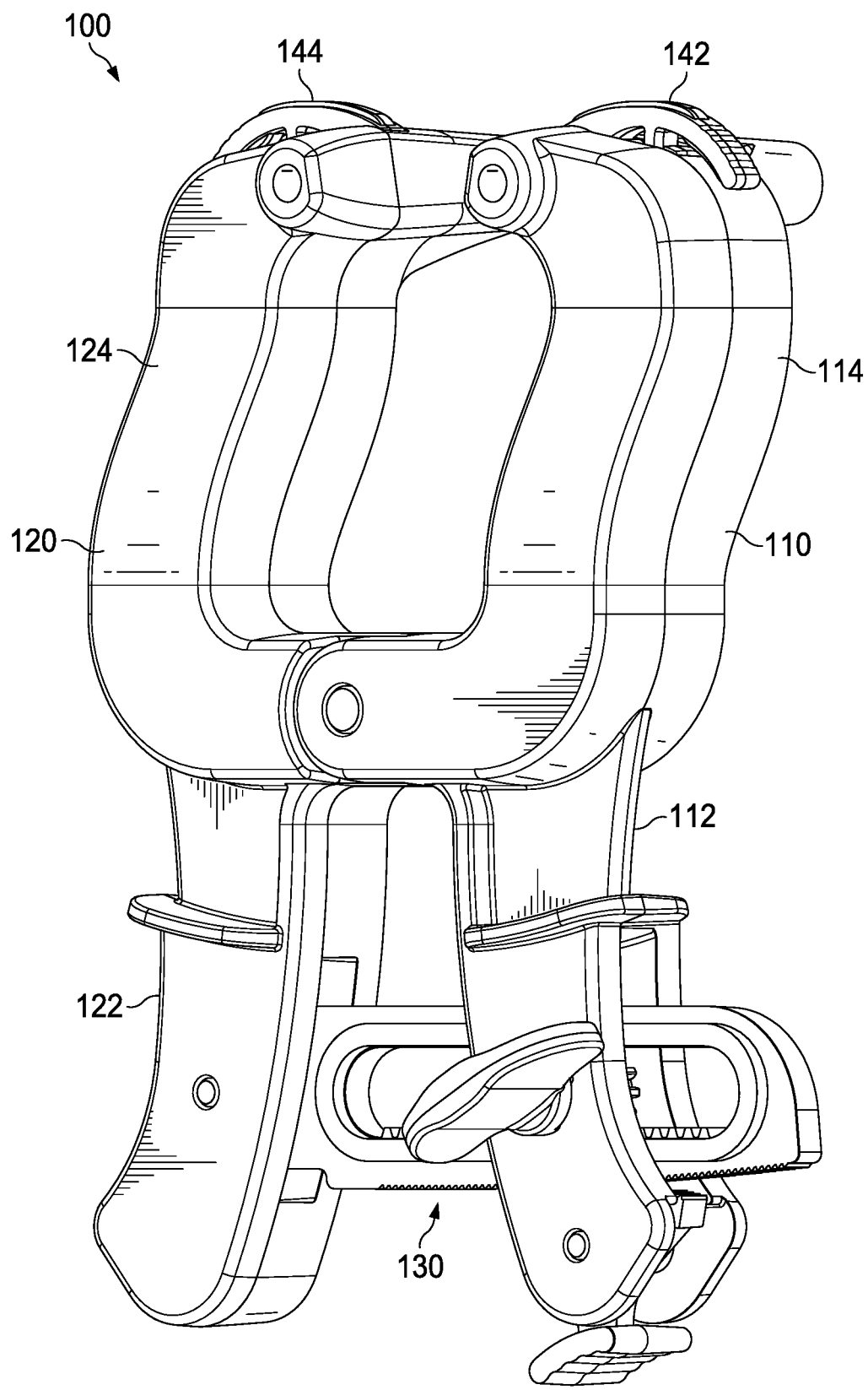
FIG. 2 is a perspective view of a front side of the polymeric vertebral retraining device of FIG. 1 in accordance with an embodiment of the present disclosure.

FIG. 3 is a rear perspective view of the device 100 shown in FIGS. 1 and 2. Accordingly, FIG. 3 illustrates many of the same features shown and discussed above with respect to FIGS. 1 and 2, including the handles 112, 122, the jaw members 114, 124, the locking assembly 130, the pin receiving members 116, 126, and the pin engaging members 142, 144. As explained above, the monolithic first and second bodies 110, 120 may be formed of a polymer or plastic. In some aspects, the bodies 110, 120 may be manufactured by injection molding. In some aspects, injection molding large, solid bodies may be challenging. As the thickness of a molded body's components increase, the amount of material required also increases, as well as the time the molded body remains in the mold after injection for cooling. Further, large, solid bodies may be susceptible to warping or deformation during cooling, and an increased risk of voids or other defects in the molded structure that may compromise the strength or structural integrity of the component. It may be desirable to reduce the thickness of the components (e.g., sidewalls) to avoid some of these issues. However, reducing the thickness or cross-sectional area of the component may also make the component weaker or less rigid. The embodiments described herein, as illustrated in FIG. 3, for example, may be suitable for injection molding by reducing solid material thicknesses while maintaining the strength and rigidity of the device 100.

As shown in FIG. 3, each of the monolithic bodies 110, 120 comprise geometries having various cavities, rib structures or patterns, and recesses which can reduce the material thickness at one or more locations in the bodies 110, 120. Notably, each of the bodies 110, 120 includes a webbing or rib structure 150 comprising a network of ribs that intersect and connect to one another, while leaving recesses or spaces between the ribs to reduce material thickness. In the illustrated embodiment, the rib structures 150 comprise diamond patterns. However, it will be understood that the present disclosure contemplates other types of patterns as well, including honeycomb or hexagonal patterns, octagonal patterns, checkerboard patterns, circular patterns, triangular patterns, and/or any other suitable pattern.

The rib structures 150 occupy an interior space of the jaw members 114, 124 of each of the bodies 110, 120. The top and lateral surfaces of the jaw members 114, 124 include solid surfaces which occlude and support the rib structures 150. In other embodiments, jaw members 114, 124 may not include solid surfaces on the top and/or lateral sides of the jaw members 114, 124. For example, in some embodiments, the rib structures 150 may be visible from the front side (shown in FIG. 2) and the rear side (shown in FIG. 3). In other embodiments, an additional plate may be attached to the rear side of the jaw members 114, 124 to enclose the rib structures 150, such that the rib structures 150 are not visible from any side of the device 100.

The first and second bodies 110, 120 include additional recesses and reduced-thickness regions in the handles 112, 122. For example, the second body 120 includes a recess 160 at a proximal region of the handle 122 below the locking assembly 130. In this regard, the handle 122 includes a cavity or slot configured to receive a first end of the rack 132. Accordingly, the front and rear surfaces of the handle 122 on either side of the rack-receiving slot may have a reduced thickness. However, in the region proximal of the rack-receiving slot, the recess 160 is included to reduce the material thickness. A ridge 121 outlines a portion of the handle 122 to provide increased rigidity and support around the recessed structure. The distal portions of the handles 112, 122 include I-beam structures, which also reduce material thickness. The I-beam structures may be associated with a width 118. Because the larger forces will be experienced by the handles 112, 122 in the direction of the width 118, the thickness of the material may be greater in the direction of the width 118 than in the depth direction (e.g., 111, FIG. 4) of the bodies 110, 120. In some embodiments, the handles 112, 122 may include similar rib structures as the structures 150 in the jaw members 114, 124.

The recesses, cavities, and rib structures 150 described herein may maintain the material thickness at any given location within the first and second bodies 110, 120 to an amount conducive to injection molding, casting, or other polymer-based manufacturing processes. For example, in some aspects, the thicknesses of the rib structures may range between 4 mm and 0.5 mm, including values such as 1.0 mm, 1.5 mm, 1.8 mm, 2.0 mm, 2.2 mm, or any other suitable value. Similarly, the solid exterior surfaces and handle portions may have thicknesses ranging between 5 mm and 0.5 mm, including values such as 1.0 mm, 1.5 mm, 2.0 mm, 2.5 mm, 3.0 mm, 3.5 mm, or any other suitable value. Thus, although the cross-sectional profile or footprint of the device may be relatively large or thick, the solid material thickness at any location may be relatively thin. For example, although the thickness or depth 111 of the jaw members 114, 124 may be between 10 mm-30 mm and the width 128 may be similarly dimensioned, the rib structure design defines voids and spaces so that the solid material thickness may be 0.5 mm-5.0 mm, for example.

The first and second bodies 110, 120 are formed with integral coupling features, such as hinge pin receiving apertures for the hinge pin 106, the pin receiving members 116, 126, and locking assembly connecting features in the handles 112, 122. As explained further below with respect to FIG. 6, the integrated connecting features of the first and second monolithic bodies 110, 120 may simplify assembly, reduce complexity, and improve the robustness of the device 100.

FIG. 4 is a side elevation view of the device 100, showing a lateral side of the first monolithic body 110. As shown, the first monolithic body 110 includes a downward curve in a transition region 170 of the first body 110. The second body 120 includes a similar downward curve. The curve in the transition region 170 may advantageously make raise the handles 112, 122 to make them more accessible to the user while extending the downward reach of the pin receiving members 116, 126 to receive and encompass the protruding portions of the pins 50. The pin receiving member 116 includes a bottom opening 115 through which a pin 50 is received in the pin receiving member 116. The first body 110 includes a depth or thickness 111 in the vertical direction of FIG. 4. The depth or thickness 111 may be between 15 mm and 30 mm, in some embodiments. The depth 111 may be constant, or approximately constant across the length of the first body 110, including the transition region 170.

A portion of the locking assembly 130 is positioned within a slot formed in the first body 110. For example, a portion of the thumbscrew actuator 134 and the rack 132 may be operably coupled to the first body 110 and positioned within the slot of the handle 112 of the first body 110.

Each of the first body 110 and the second body 120 include a plurality of buttresses or supports extending from the bottom surface of the jaw members 114, 124 and along the external surface of the pin receiving members 116, 126. The supports, which may individually have small thicknesses, provide additional strength and rigidity of the pin receiving members 116, 126 to reduce the amount of flexing or splaying. The supports may be positioned around a portion of the circumferences of the pin receiving members 116, 126. For example, the supports may be distributed around approximately a quarter of the circumferences of the pin receiving members 116, 126, but are excluded from the inner sides of the pin receiving members 116, 126 to provide access to the surgical site. Further, in the illustrated embodiment, the pin receiving members 116, 126 have tapered thicknesses such that the members 116, 126 are thicker (and therefore more rigid) at the base of the jaw members 114, 124, and thinner toward the distal ends of the members 116, 126 at the openings 115, 125.

Figure 5A:
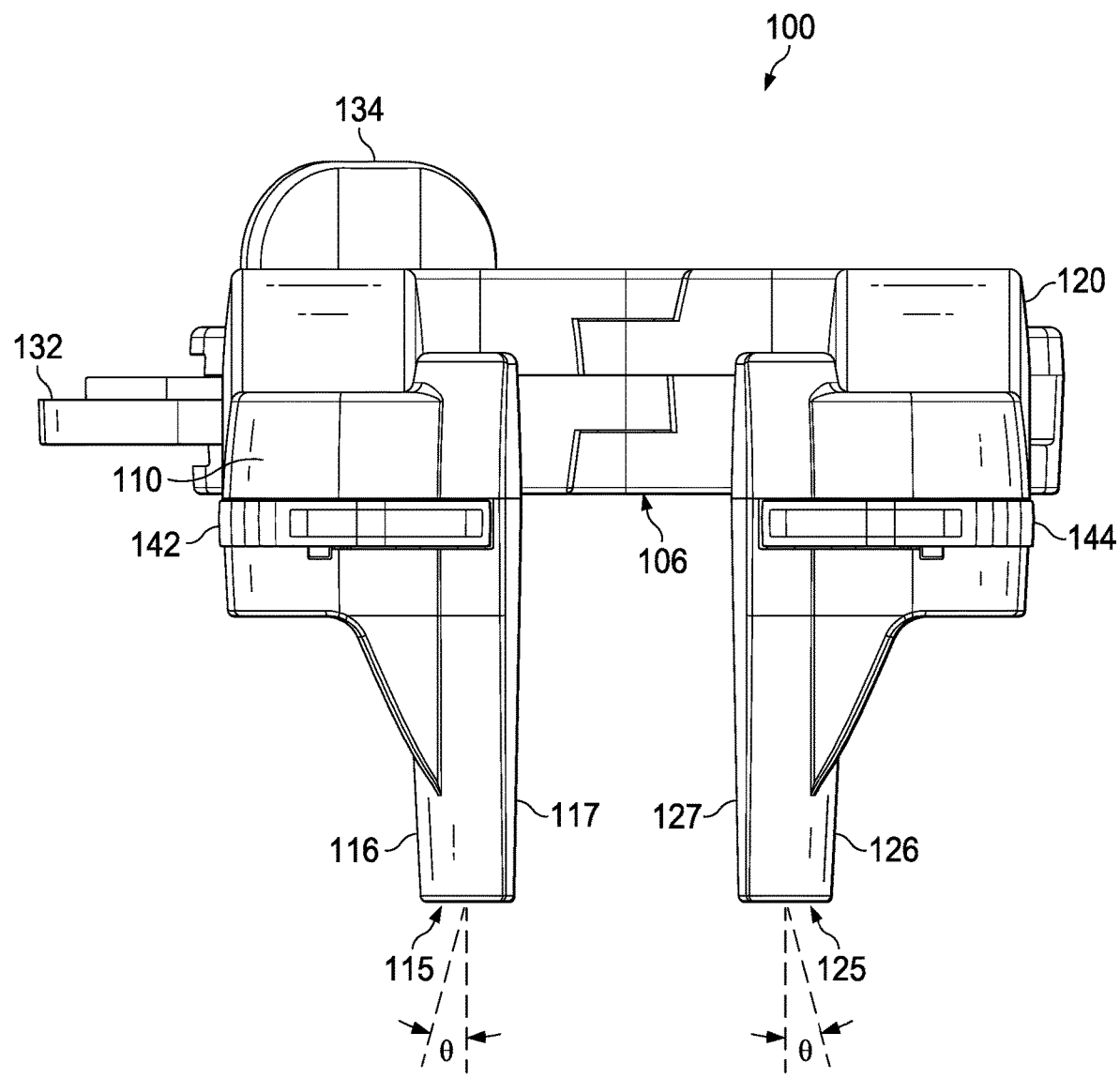
FIG. 5A is an elevation view of a distal side of the polymeric vertebral retraining device of FIG. 1 in accordance with an embodiment of the present disclosure.
Figure 5B:
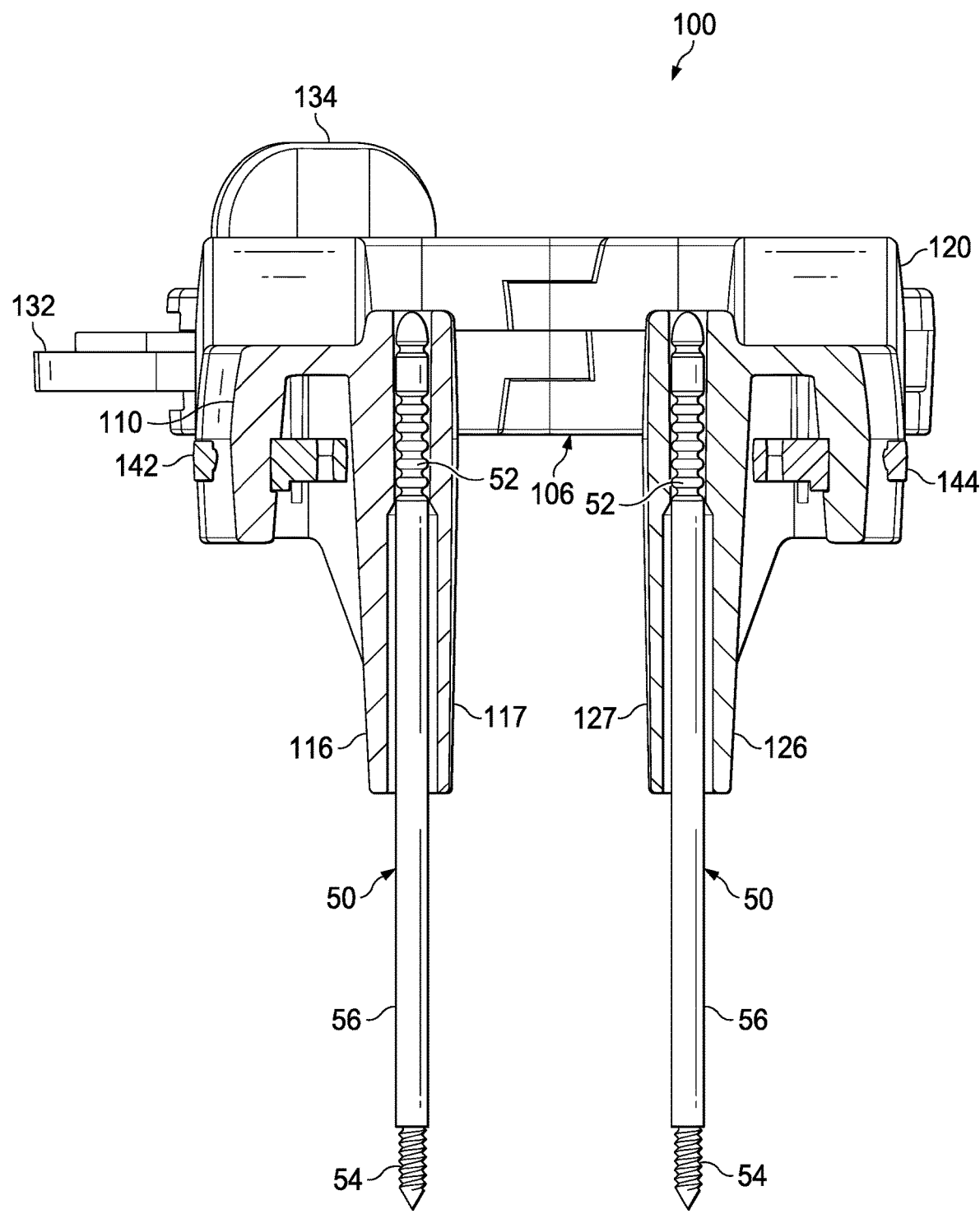
FIG. 5B is a cross-sectional view of the distal side of the polymeric vertebral retraining device as shown in FIG. 5A with pins inserted in accordance with an embodiment of the present disclosure.
Figure 5C:
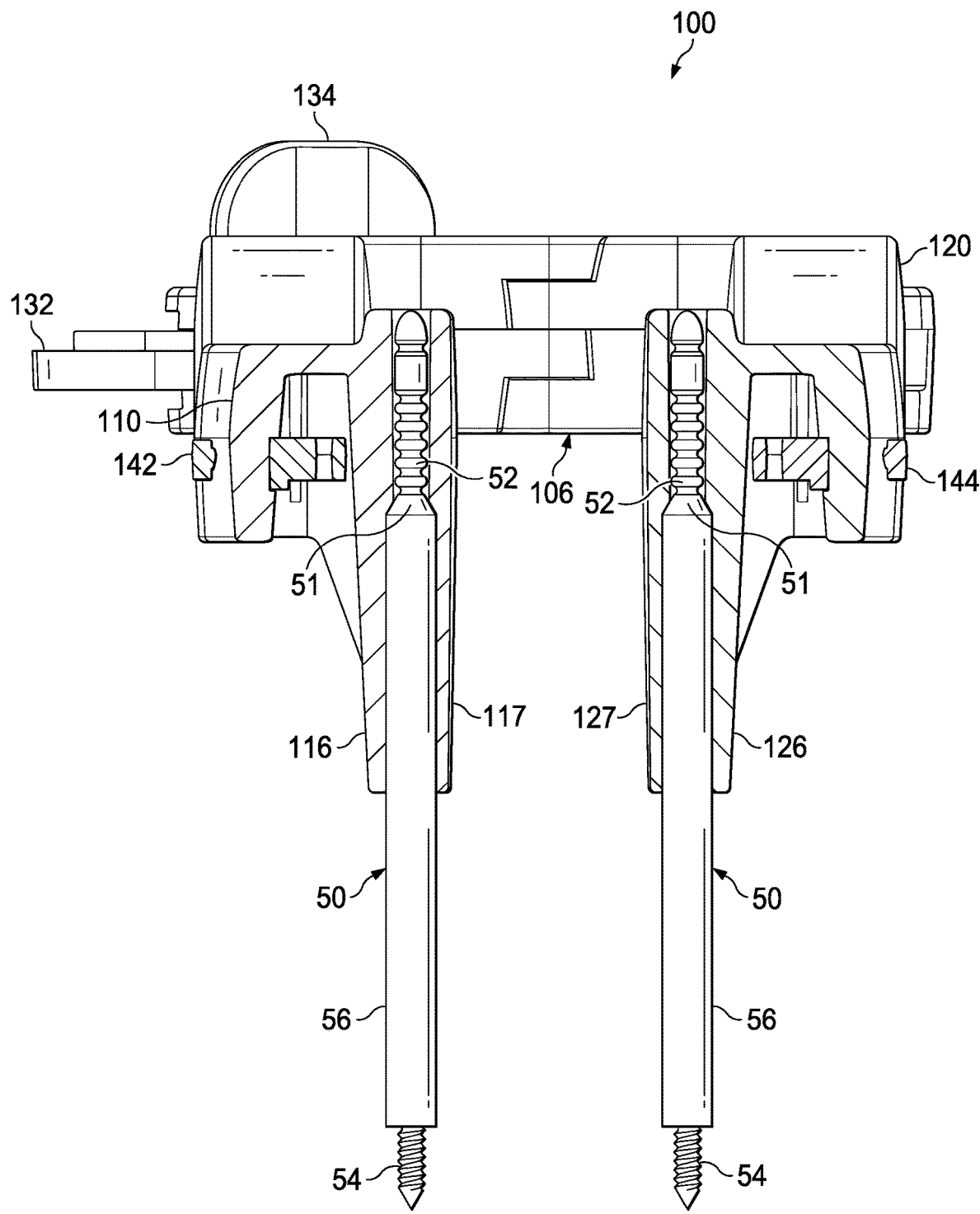
FIG. 5C is a cross-sectional view of the distal side of the polymeric vertebral retraining device as shown in FIG. 5A with pins inserted in accordance with an embodiment of the present disclosure.
Figure 5D:
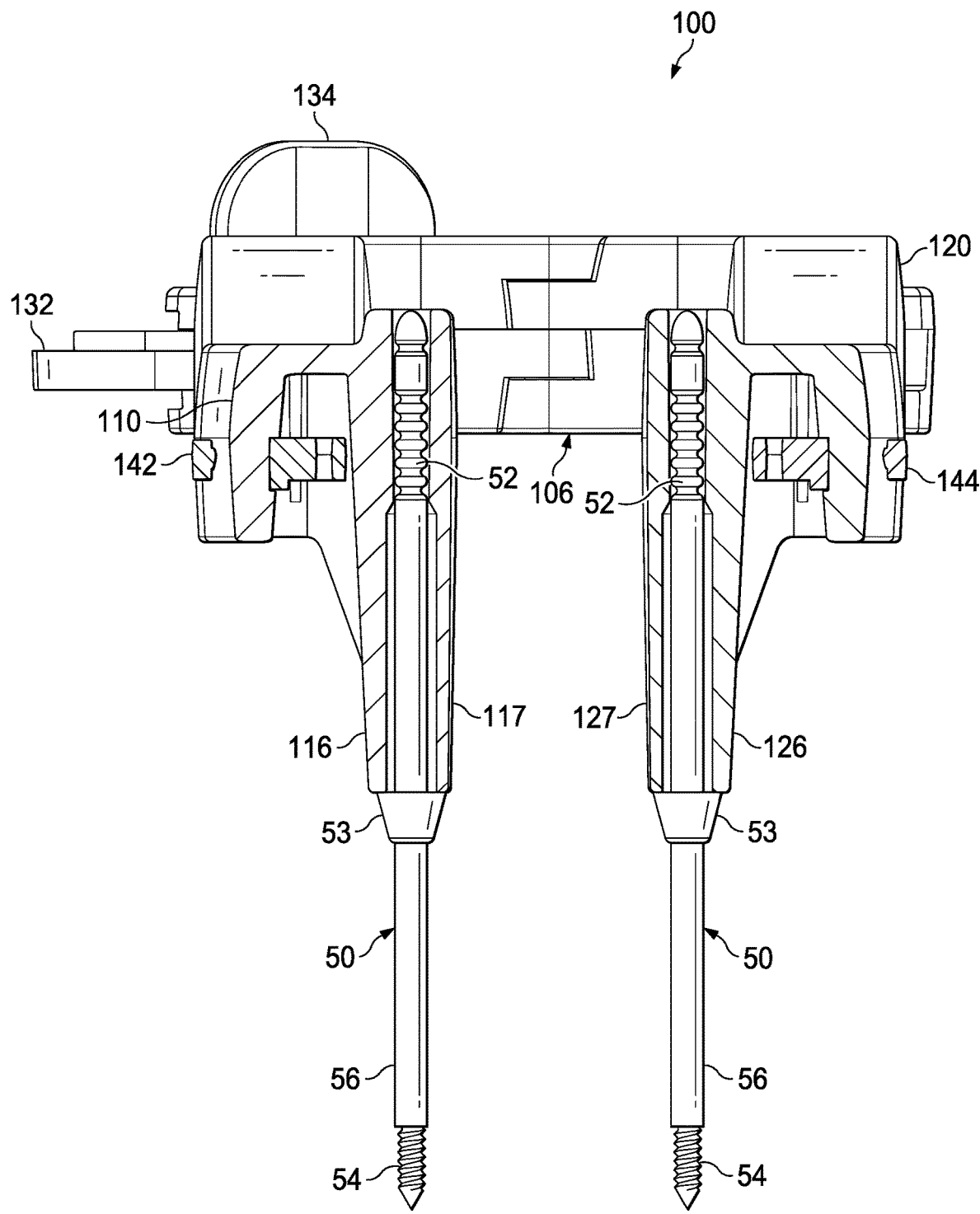
FIG. 5D is a cross-sectional view of the distal side of the polymeric vertebral retraining device as shown in FIG. 5A with pins inserted in accordance with an embodiment of the present disclosure.

FIGS. 5A-5D illustrate a top or distal side of the device 100. FIG. 5A illustrates the device 100 with no pins inserted into the pin receiving members. FIGS. 5B-5D illustrate the device 100 with pins inserted into the pin receiving members 116, 126, according to various embodiments of the present disclosure. Referring to FIG. 5A, the first and second bodies 110, 120, including the pin receiving members 116, 126, are shown. FIG. 5A further shows the thumbscrew actuator 134 and rack 132 of the locking assembly and the pin engaging members 142, 144. The first body 110 interlocks with the second body 120 via the hinge 106. The pin receiving members 116, 126 include corresponding flat surfaces 117 and 127 on inner sides of the pin receiving members 116, 126. The flat surfaces 117, 127 may reduce the sidewall thickness or profile of the pin receiving members 116, 126 to increase access to the space between the pin receiving members 116, 126. In this regard, it will be understood that the center of the surgical site may reside directly between the pin receiving members 116, 126, which are coupled to corresponding pins driven into the vertebrae. Each pin receiving member 116, 126 includes a corresponding opening 115, 125 through which the protruding portion of the pin is received into the device 100.

The pin receiving members 116, 126 may be coupled to the pins such that the pins may rotate within the pin receiving members 116, 126. Accordingly, pin engaging members 142, 144 may retain the pins within the pin receiving members 116, 126 in the vertical axis of FIG. 5A, but may not limit rotational movement of the pins within the pin receiving members 116, 126. In the illustrated embodiment, the pin receiving members 116, 126 may extend directly vertical and in parallel. In other embodiments, each the pin receiving members 116, 126 may include a splay angle θ in an outward direction such that the bottom ends of the pin receiving members 116, 126 (near the openings 115, 125) are angled slightly away from one another. Accordingly, in some embodiments, the pin receiving members 116, 126 may be non-parallel. For example, the angle formed between the respective axes of the pin receiving members 116, 126 (2*θ) may range from 2° to 10°, including angles of 3°, 4°, 5°, 6°, 7°, or any other suitable angle, greater or smaller.

FIG. 5B shows the device 100 of FIG. 5A, with pins 50 inserted into the pin receiving members 116, 126. In the embodiment of FIG. 5B, the pins 50 include a plurality of grooves 52 that can engage with the pin engaging members 142, 144 to retain each of the pins 50 at a different depth within the pin receiving members 116, 126. The pins 50 further include a bone screw portion 54 configured to be driven into the vertebrae. The pins 50 further include spacer portions 56 between the grooves 52 and the bone screw portions 54 such that the pin receiving members 116, 126 are spaced from the vertebrae.

In some aspects, it may be beneficial to provide a minimum insertion depth of the pins 50 within the pin receiving members 116, 126. For example, the pins 50 may include one or more depth stop features such that the grooves 52 of the pins 50 are maintained within an engagement region to engage with the pin engaging members 142, 144. FIGS. 5C and 5D illustrate the device 100 and pins 50 with depth stop features. It will be understood that the embodiments illustrated in FIGS. 5C and 5D are examples and that the embodiments may be modified and/or combined without departing from the scope of the present disclosure.

FIG. 5C shows the device 100 of FIG. 5A, with pins 50 inserted into the pin receiving members 116, 126. In the embodiment of FIG. 5C, the pins 50 include the grooves 52, bone screw portions 54, and the spacer portions 56, as similarly shown in FIG. 5B. Additionally, the screws 50 in FIG. 5C include tapered sections 51 configured to engage corresponding tapered surfaces within the pin receiving members 116, 126. The tapered sections 51 comprise transitions in thicknesses between the grooves 52 and the spacer portions 56. Accordingly, the pins 50 can be inserted into the pin receiving members 116, 126 and advanced until the conical shaped tapered sections 51 contact the corresponding tapered surfaces inside the pin receiving members 116, 126.

FIG. 5D shows the device 100 of FIG. 5A, with pins 50 inserted into the pin receiving members 116, 126. In the embodiment of FIG. 5D, the pins 50 include the grooves 52, bone screw portions 54, and the spacer portions 56, as similarly shown in FIG. 5B. Additionally, the screws 50 in FIG. 5C include shoulders 53 configured to engage the distal surfaces of the pin receiving members 116, 126. The shoulders 53 comprise conical shapes extending outward from the spacer portions 56. Accordingly, the pins 50 can be inserted into the pin receiving members 116, 126 and advanced until the conical shaped shoulders 53 contact the distal surfaces of the pin receiving members 116, 126. In some embodiments, the shoulders 53 may be adjustable such that the minimum depth or distance of the pins 50 can be adjusted within an adjustment range. In other embodiments, the shoulders 53 are fixed to the pins 50. In some embodiments, the shoulders 53 are an integral and/or monolithic feature of the pins 50. For example, the pins 50 may be machined to include the shoulders 53.

Figure 6:
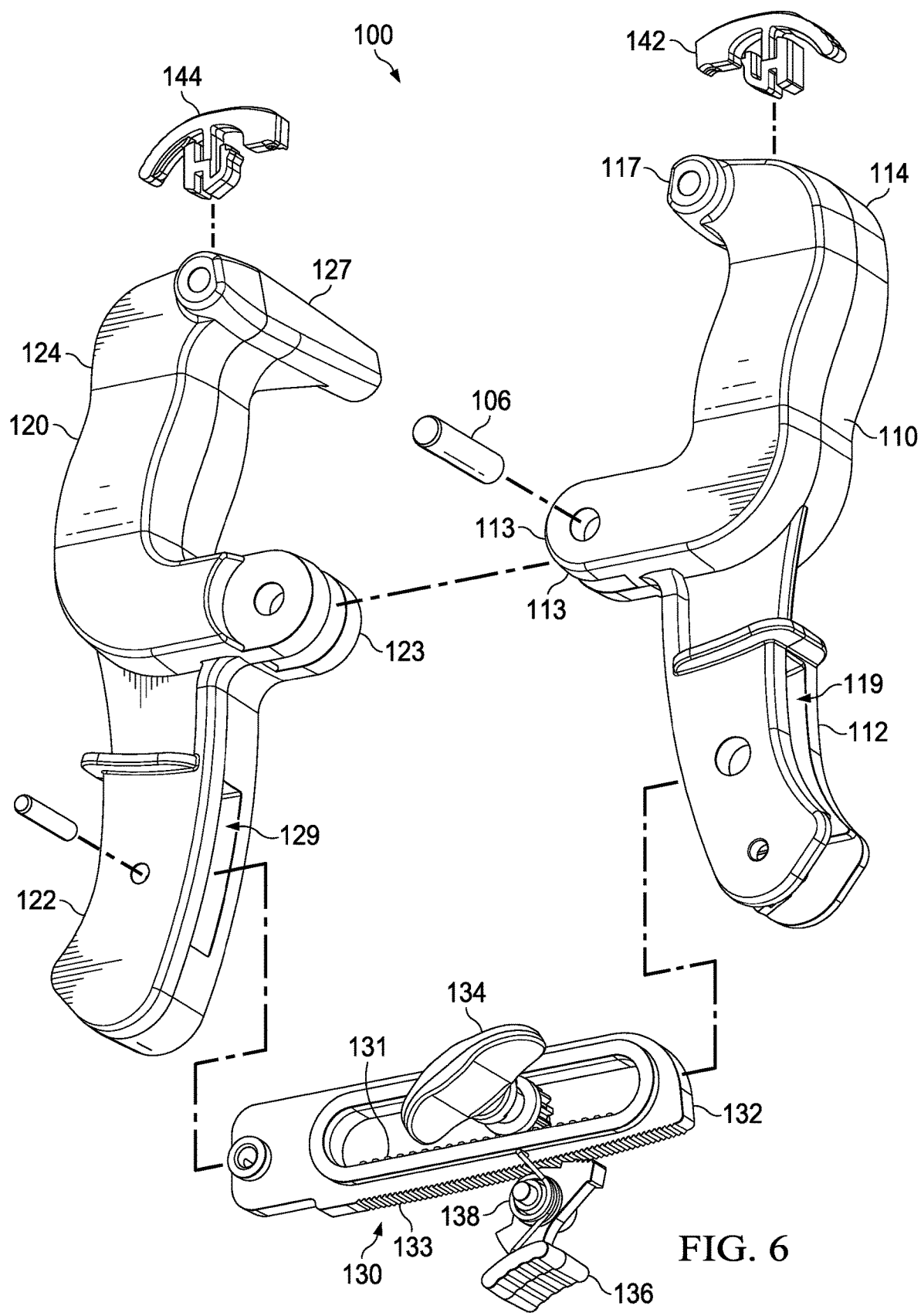
FIG. 6 is a perspective exploded view of the polymeric vertebral retraining device of FIG. 1 in accordance with an embodiment of the present disclosure.

FIG. 6 is an exploded view of the device 100 shown above in FIGS. 1-5. Referring to FIG. 6, the device 100 includes a monolithic first body 110, and a monolithic second body 120. The monolithic first body 110, for example, includes a handle 112, a jaw member 114, and a pin receiving member 116. The first body 110 further includes a coupling portion 113 configured to couple with a corresponding coupling portion 123 of the second body 120. When the coupling features 113, 123, which are positioned between corresponding handles 112, 122 and jaw members 114, 124, engage and interlock with one another, a hinge pin 106 can be positioned within hinge apertures in the coupling features 113, 123 to form a pivoting hinge mechanism of the device 100. The apertures of the coupling features 113, 123 and the hinge pin 106 may be formed such that the hinge pin 106 is locked or retained with in the hinge apertures of the features 113, 123 without additional fasteners, set screws, adhesives, or other components. Accordingly, the assembly process may be simplified. In other embodiments, adhesives or other fasteners may be used to retain the hinge pin 106 in place.

The entirety of the first body 110 may be monolithically or integrally formed such that the handle 112, the coupling feature 113, the jaw member 114, and the pin receiving member 116 form a unitary, monolithic body that can be formed by injection molding using a single mold, for example. Similarly, the entirety of the second body 120 may be monolithically or integrally formed such that the handle 122, the coupling feature 123, the jaw member 124, and the pin receiving member 126 form a unitary, monolithic body that can be formed by injection molding using a single mold. By reducing the number of individual components, the manufacturing cost and complexity may decrease. Further, the probability of assembly errors or defects may decrease, as well as the mechanical "slop" associated with complex assemblies. This may increase the feasibility of single-use operation, which reduces other costs of sterilization and storage at the surgical center. Further, if the device 100 is configured for multiple uses, the unitary design of the bodies 110, 120 may facilitate sterilization.

The first handle 112 defines a first slot 119 for the locking assembly 130, and the second handle 122 defines a second slot 129. The slots 119 may be dimensioned to receive and house respective portions of the locking assembly 130, such that the locking assembly 130 operates on a plane extending through a center depth region of each handle 112, 122. The handles 112, 122 also define coupling or fastening features, such as apertures, to connect the components of the locking assembly 130 to the handles 112, 122. For example, a fastener may be positioned through a first fastener aperture in the second handle 122 to couple a first end of the rack 132 to the second handle 122. The thumbscrew actuator 134 may be positioned to extend through a second aperture in the first handle 112 such that the thumbscrew actuator 134 engages the rack 132 through the second aperture. The slots 119, 129 may be long enough to allow for some rotation of the rack 132 about the respective apertures. In this regard, because the first body 110 is coupled to the second body 120 via a pivoting hinge 106, the expansion or contraction of the handles 112, 122 occurs in an arc rather than a straight line. Accordingly, the connection between the locking assembly 130 and the body is 110, 120, may allow for rotation of at least the rack 132 within the slots 119, 129.

Each of the pin engaging members 142, 144 includes a unitary or monolithic component. For example, the pin engaging members 142, 144 may be formed by injection molding. In one example, the pin engaging members 142, 144 are identical. In other embodiments, the pin engaging members 142, 144 may be unique in one or more aspects. The pin engaging members 144, 142 may include a living hinge or plastic spring such that the pin engaging members 142, 144 can be individually actuated by flexing a portion of the pin engaging members 142, 144 to disengage the pin engaging members 142, 144 from the corresponding pins. The pin engaging members 142, 144 will be further described in FIG. 8.

Figure 7:
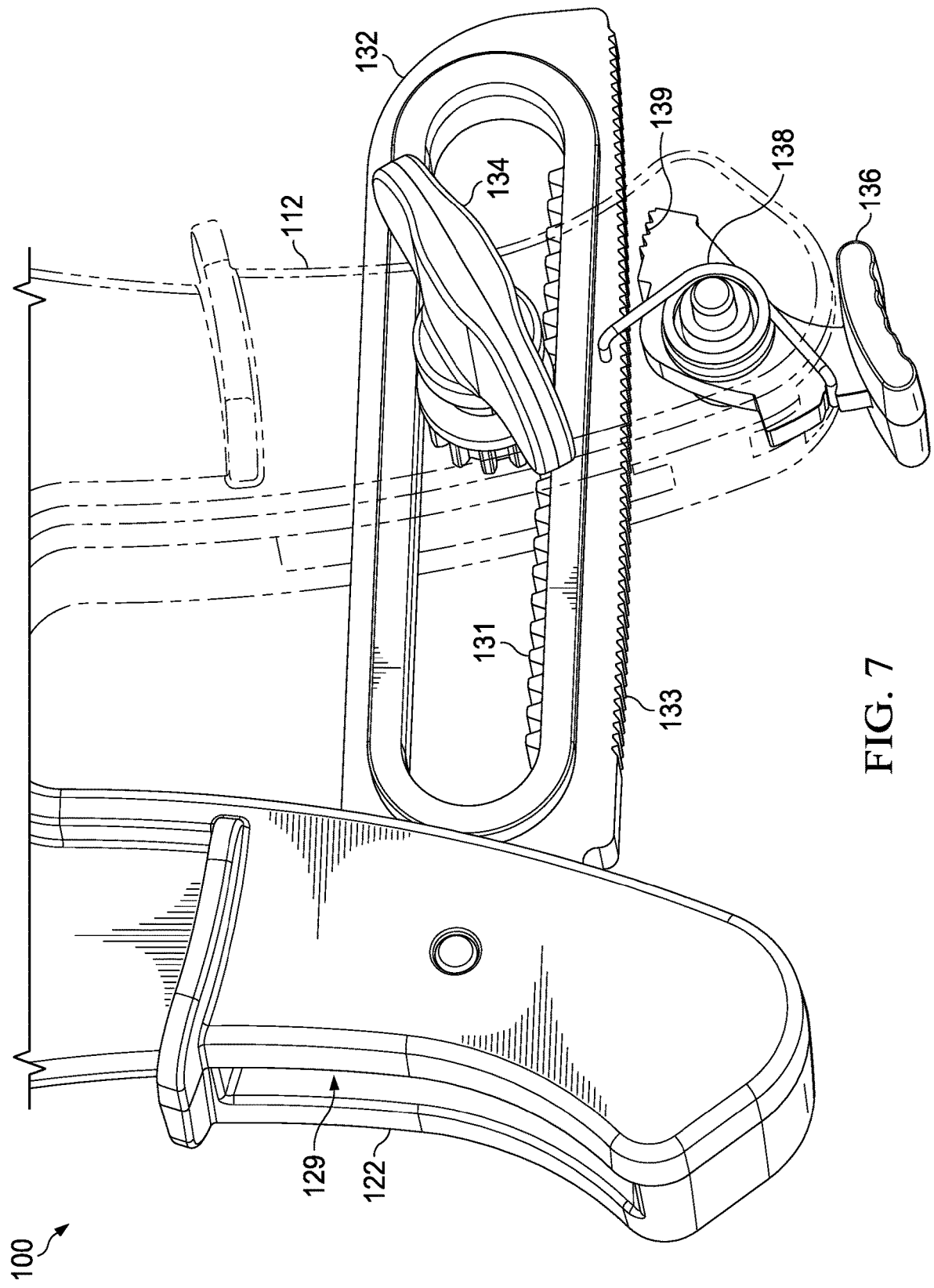
FIG. 7 is a partially transparent perspective view of a locking assembly and handle region of the polymeric vertebral retraining device of FIG. 1 in accordance with an embodiment of the present disclosure.

Referring to FIGS. 6 and 7, the locking assembly 130 includes the thumbscrew actuator 134, the rack 132, a ratchet member 136, and a spring 138. The rack 132 includes a set of inner teeth 131 and a set of outer teeth 133. The set of inner teeth 131 are configured to engage with the pinion gear teeth of the thumbscrew actuator 134 to cause expansion or contraction of the handles 112, 122. In other words, the thumbscrew actuator 134 and the rack 132 form a rack-and-pinion mechanism to effect a linear force between the handles 112, 122. The set of outer teeth 133 of the rack 132 are configured to engage ratchet teeth 139 on the ratchet member 136. When engaged, the second set of teeth 133 and the ratchet teeth 139 of the ratchet member 136 provide for movement of the rack 132 relative to the ratchet member 136 in a first direction, but not in a second direction. For example, each of the second set of teeth 133 and the ratchet teeth 139 of the ratchet member 136 may include a sawtooth pattern or similar pattern that allows for movement in one direction but not the other. In other embodiments, the second set of teeth 133 and the teeth 139 may be configured to disallow movement in either direction until the ratchet member 136 is disengaged.

In the illustrated embodiment, the second set of teeth 133 and the ratchet teeth 139 of the ratchet member 136 allow for movement in the contraction direction (handles moving toward each other, pin receiving members moving away from one another) but not in the expansion direction. In other embodiments, the second set of teeth 133 and the ratchet teeth 139 of the ratchet member 136 may allow for movement in the expansion direction, but not in the contraction direction. The spring 138 is coupled to the ratchet member 136 and the rack 132, and biases the ratchet member 136 such that the ratchet teeth 139 engage the second set of teeth 133. The ratchet member 136, however, can be selectively disengaged from the second set of teeth 133 to allow movement of the handles 112, 122 in either direction. The ratchet member 136 can be disengaged from the rack 132 by articulating a lever portion of the ratchet member 136 inward toward the second handle 122, similar to a switch. The ratchet member 136 is coupled to the first handle 112 by a third aperture defining an axis, about which the ratchet member 136 can rotate.

Figure 8:
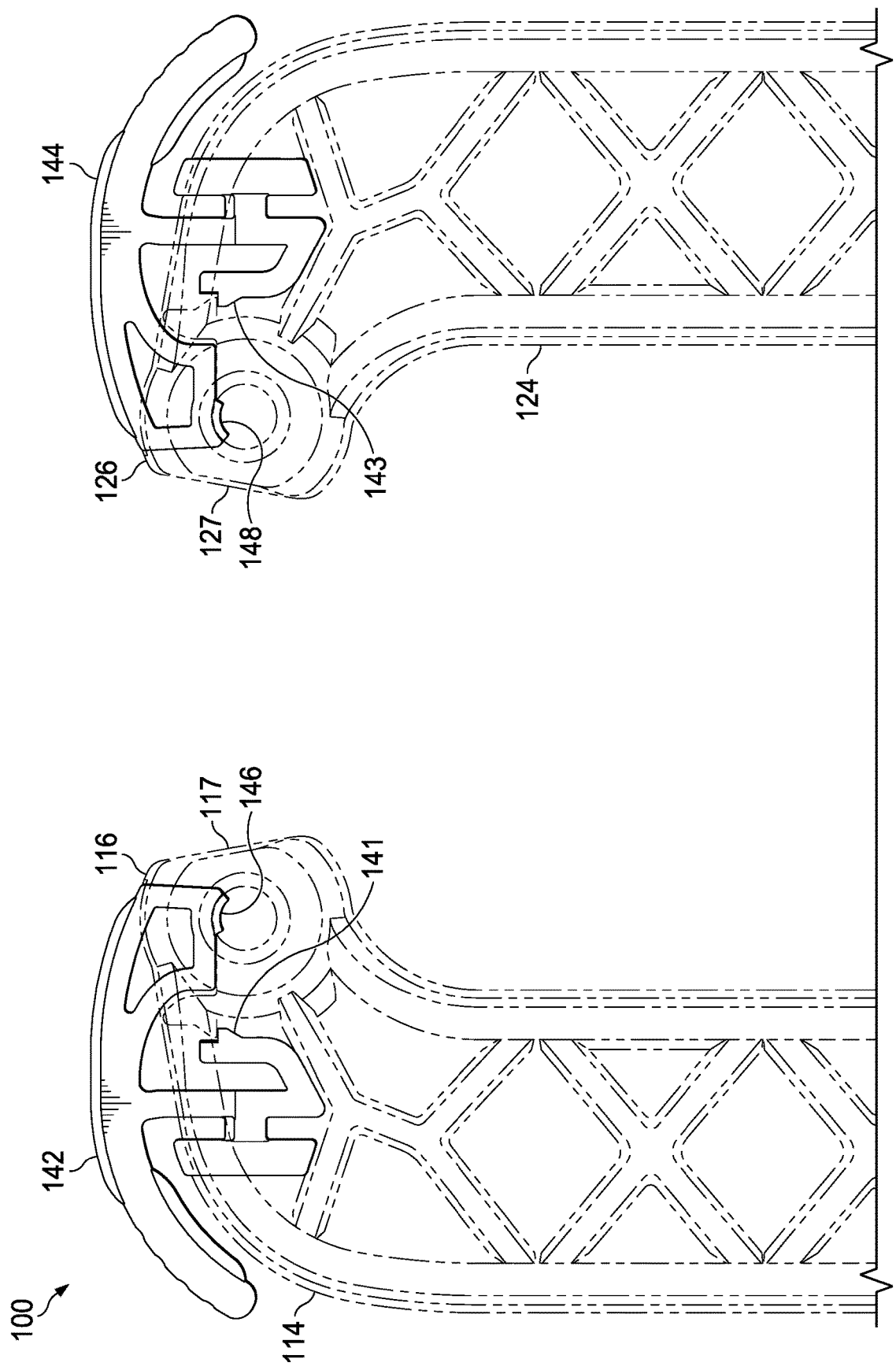
FIG. 8 is a partially transparent perspective view of pin engaging members and a jaw region of the polymeric vertebral retraining device of FIG. 1 in accordance with an embodiment of the present disclosure.

FIG. 8 is a top elevation view of a distal region of the device 100, including jaw members 114, 124, and the first and second pin engaging members 142, 144. The pin engaging members 142, 144 are positioned within respective cavities of the first body 110 and the second body 120. The first pin engaging member 142 includes a first locking tab 146, and the second pin engaging member 144 includes a second locking tab 148. The locking tabs 146, 148 are configured to engage a corresponding groove in the protruding portion of the respective pins, while allowing at least some rotation of the pins within the pin receiving members 116, 126. The pin engaging members 142, 144 can be actuated to disengage the locking tabs 146, 148 from the respective pins by depressing outer lever portions of the pin engaging members 142, 144 downward or proximally.

In the illustrated embodiment, the pin engaging members 142, 144 include unitary, monolithic components such that the flexion of the members 142, 144 is provided by the plasticity of the material. The pin engaging members 142, 144 may comprise a material that is flexible while providing sufficient rigidity so that the pins do not become inadvertently disengaged from the locking tabs 146, 148. The first pin engaging member 142 includes a first locking feature 141, and the second pin engaging member 144 includes a second locking feature 143. The locking features 141, 143 may be configured to provide a locked coupling with a corresponding feature (e.g., ridge, slot) within the cavities of the first body 110 and the second body 120. Each of the first body 110 and the second body 120 may also include within the cavities a guiding feature to guide and align the pin engaging members 142, 144 into place and alignment so that the locking features 141, 143 properly seat or engage. Accordingly, assembly of the pin engaging features 142, 144 into the corresponding cavities of the first body 110 and the second body 120 may include inserting the locking feature portions of the members 142, 144 into the corresponding cavities until the locking features 141, 143 are engaged and locked.

It will be understood that the embodiments described above may be modified in one or more aspects without departing from the scope of the present disclosure. For example, the shapes, dimensions, number of components, and/or appearance of the embodiments described above may be modified in various ways. Further, the mechanisms of the present device, such as the hinge 106, the locking assembly 130, and the pin engaging members 142, 144 may include additional, fewer, or different features then what are specifically shown in FIGS. 1-8. In this regard, FIGS. 9-12 illustrate vertebral retaining devices according to other embodiments of the present disclosure. It will also be understood that one or more of the features shown in FIGS. 1-12 may be combined, in whole or in part, with one or more other features shown in FIGS. 1-12.

Figure 9:
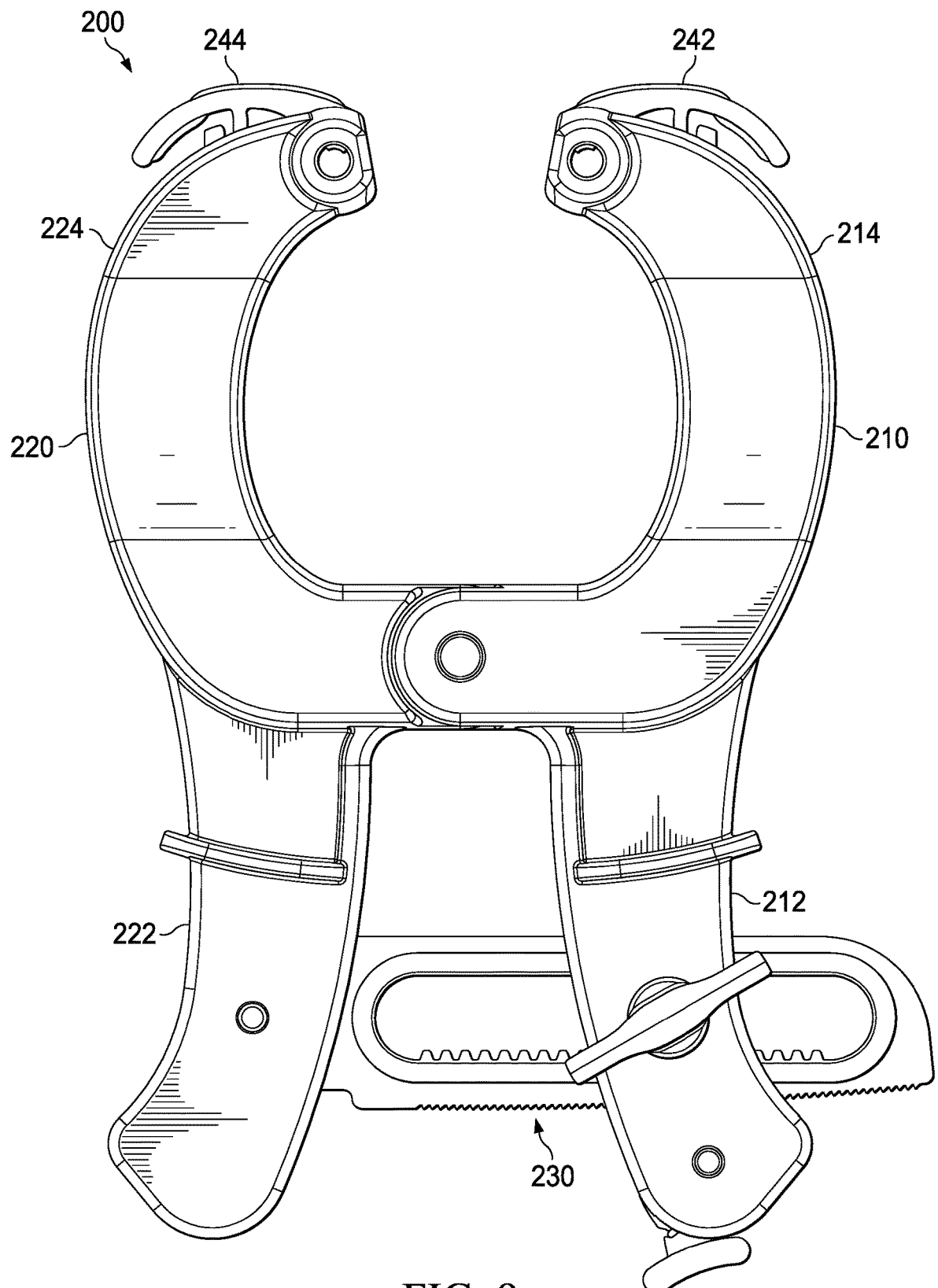
FIG. 9 is a top elevation view of a polymeric vertebral retraining device in accordance with another embodiment of the present disclosure.

FIG. 9 is a top elevation view of a vertebral retaining device 200, according to an embodiment of the present disclosure. The device 200 may include components similar or identical, in some aspects, to the device 100 shown in FIGS. 1-8. For example, the device 200 includes a first body 210 pivotably coupled to a second body 220, and a locking assembly 230. Further, the device 200 includes pin engaging members 242, 244, handles 212, 222, and jaw members 214, 224. In the embodiment of FIG. 9, the jaw members 214, 224 include curved or semi-circular shapes. The shapes of the jaw members 214, 224 may differ somewhat from the more square D-shaped profiles of the jaw members 114, 124 shown in FIGS. 1-8. In some aspects, the arcuate profile of the jaw members 214, 224 of the device 200 may provide structural or aesthetic characteristics that may be more desirable to some physicians. For example, the curved jaw members 214, 224 may provide a larger access area between the jaw members 214, 224 than the jaw members 114, 124 in the device 100.

Figure 10:
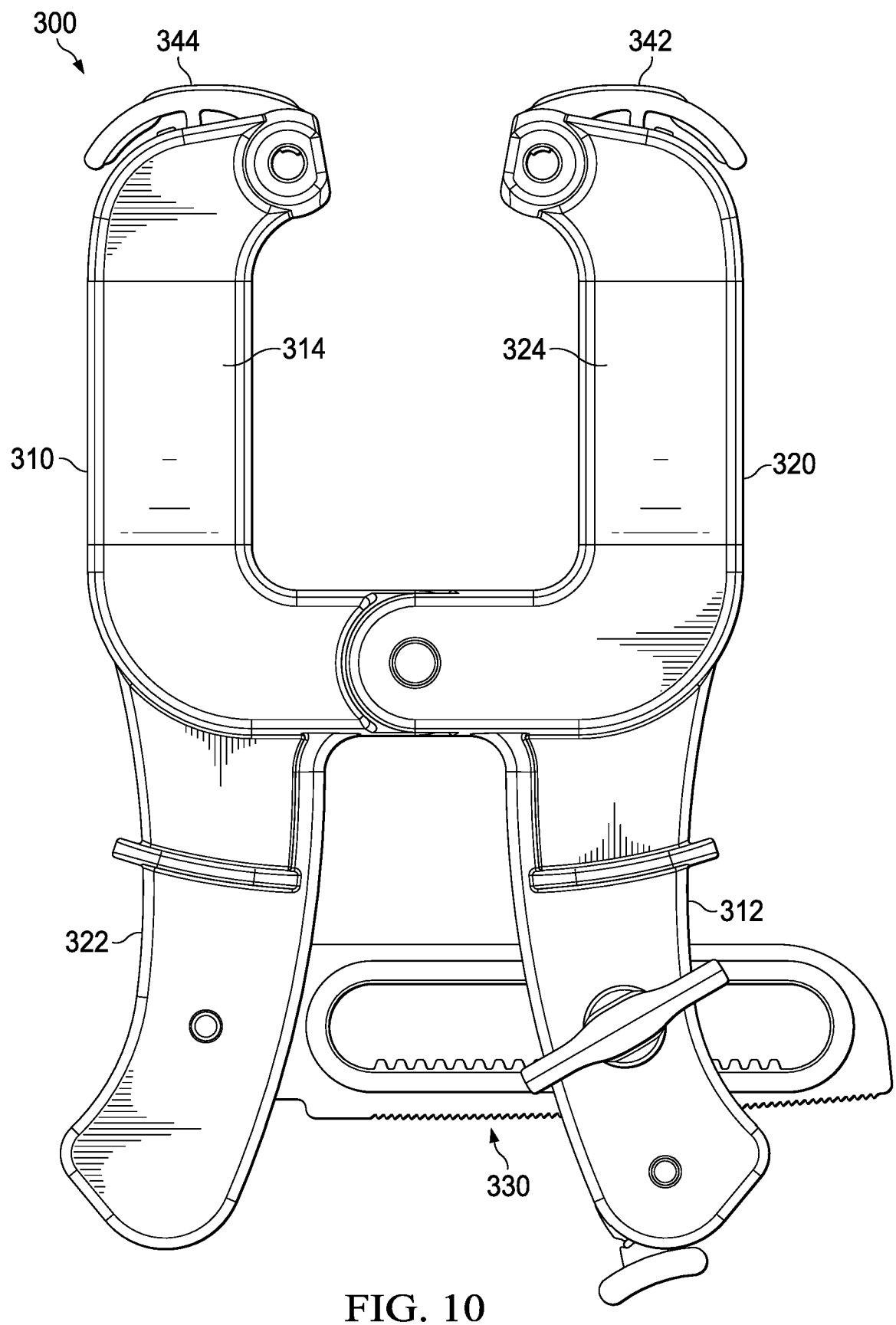
FIG. 10 is a top elevation view of a polymeric vertebral retraining device in accordance with another embodiment of the present disclosure.

FIG. 10 is a top elevation view of a vertebral retaining device 300, according to an embodiment of the present disclosure. The device 300 may include components similar or identical in some aspects to the devices 100, 200 shown in FIGS. 1-9. For example, the device 300 includes a first body 310 pivotably coupled to a second body 320, and a locking assembly 330. Further, the device 300 includes pin engaging members 342, 344, handles 312, 322, and jaw members 314, 324. In the device 300, the shapes of the first and second bodies 310, 320 have an S-shape design so that the first handle 312 of the first body 310 is on the right, and the first jaw member 314 of the first body 310 is on the left. Further, the second handle 322 of the second body 320 is on the left, and the second jaw member 324 of the second body 320 is on the right. The first and second bodies 310, 320 may be coupled to one another at a hinge 306, similar to the embodiments described above. However, the operation of the handles 312, 322 may be reversed from the operation of the handles 112, 122, for example. In this regard, expanding the handles 312, 322 also expands the jaw members 314, 324 away from one another, while squeezing or contracting the handles 312, 322 also contracts the jaw members 314, 324 toward each other.

Figure 11:
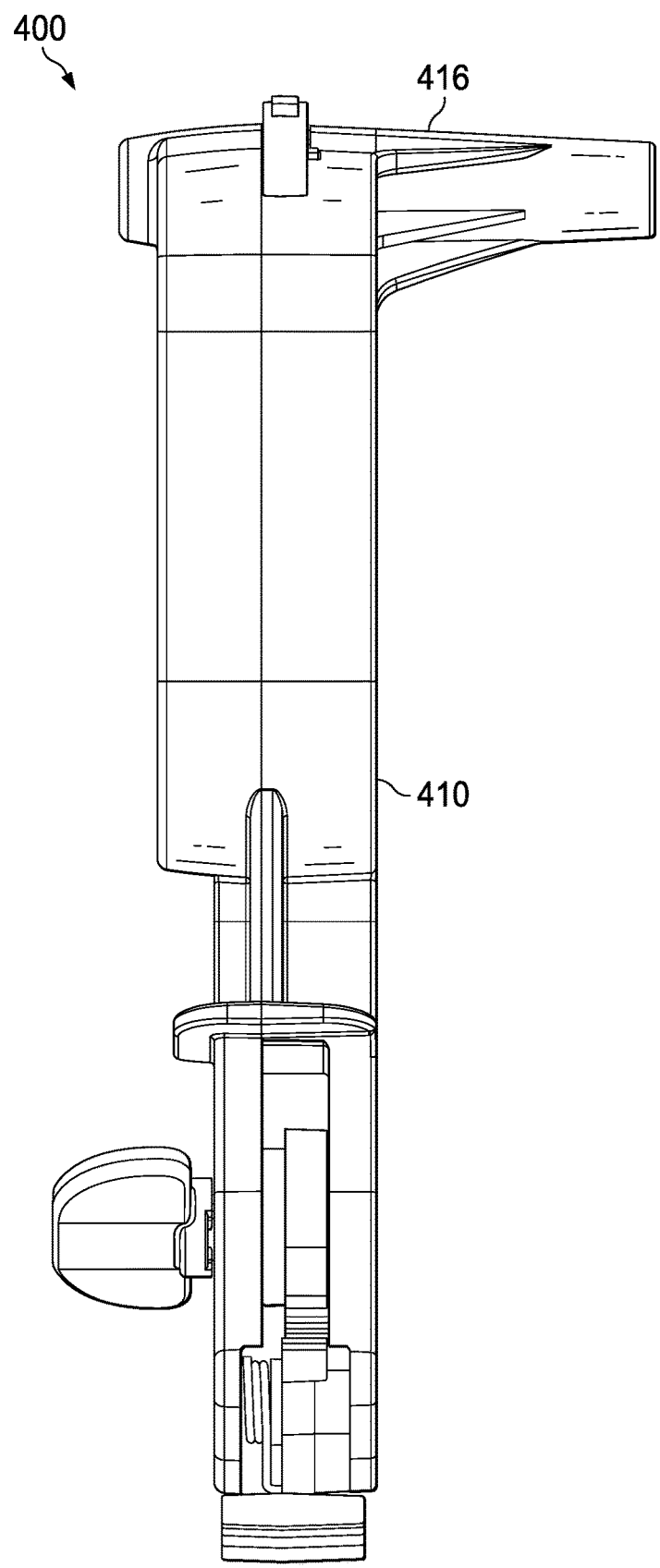
FIG. 11 is a side elevation view of a polymeric vertebral retraining device in accordance with another embodiment of the present disclosure.

FIG. 11 is a side elevation view of a vertebral retaining device 400, according to another embodiment of the present disclosure. The device 400 may be similar to the devices 100, 200, and 300 described above in one or more aspects. For example, the device 400 is shown having a first monolithic body 410, which includes a downwardly-extending pin receiving member 416 extending from a distal portion of the first body 410. The device 400 includes a straight lateral profile rather than a curved lateral profile such as the device 100, which includes a curved transition region 170 (see FIG. 4). In some aspects, the straight profile of the device 400 may be preferred by some users, and may reduce manufacturing costs or design complexity.

Figure 12:
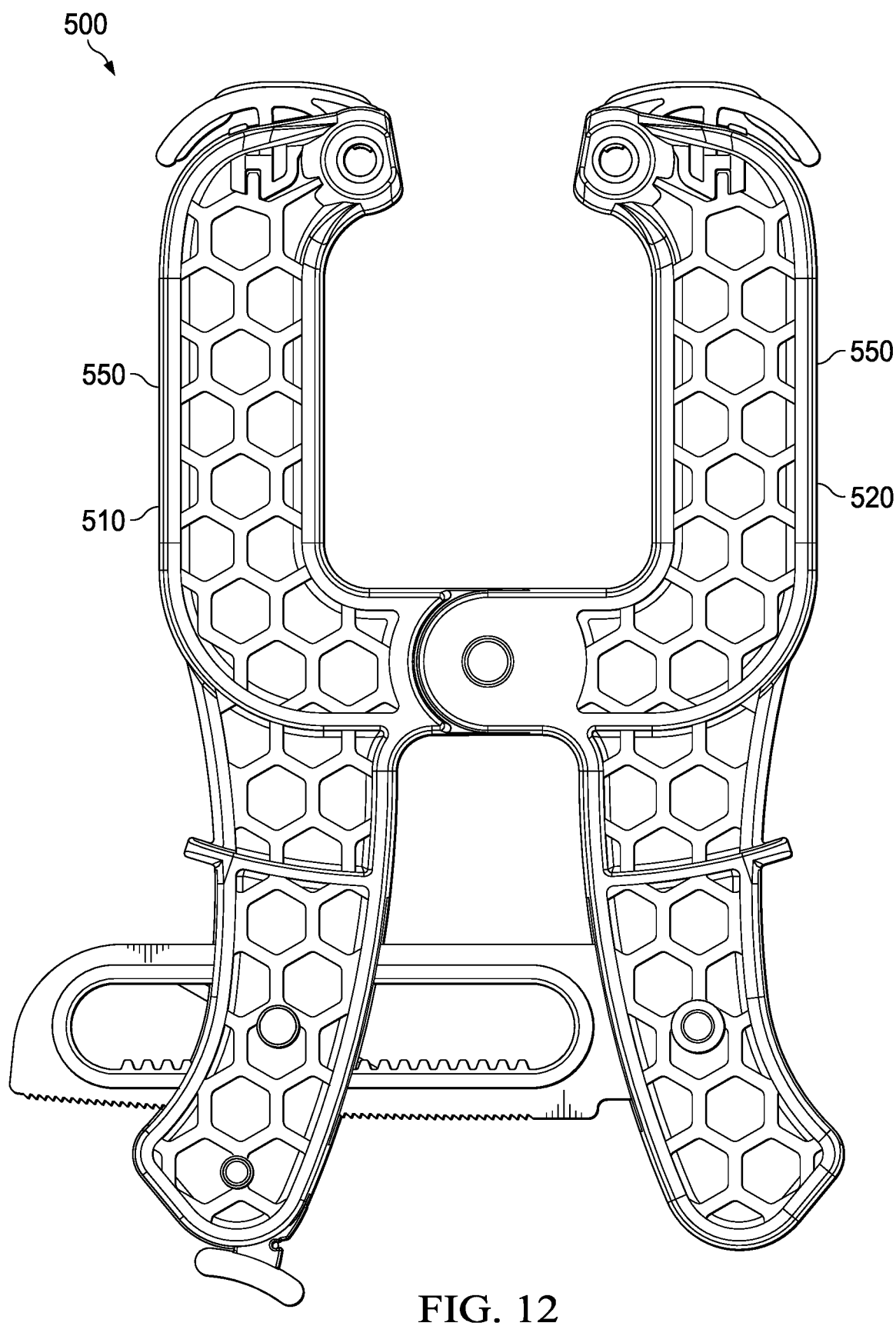
FIG. 12 is an elevation view of a rear side of a polymeric vertebral retraining device in accordance with another embodiment of the present disclosure.

FIG. 12 is a top elevation view of a rear side of a vertebral retaining device 500, according to another embodiment of the present disclosure. The device 500 may include components similar or identical in some aspects to the device 100 shown in FIGS. 1-8. For example, the device 500 includes a first body 510 pivotably coupled to a second body 520, where the first and second bodies 510, 520 include rib structures 550. In the embodiment of FIG. 12, the rib structures 550 occupy at least a portion of the handles 512, 522 in addition to the portions of the jaw members 514, 524. Further, in the embodiment of FIG. 12, the device 500 is shown with a honeycomb pattern. However, it will be understood that any suitable pattern may be used for the rib structures 550, including octagonal, square, triangular, circular, diamond, trapezoidal, serpentine, and/or any other suitable shape or combination thereof.

The devices 100, 200, 300, 400, 500, and/or the various components thereof, may be formed of one or more polymeric materials, including plastics. For example, the bodies (e.g., 110, 120), locking assembly components, pin engagement members, hinge pins, fasteners, and/or any other suitable component, may comprise a polymer. In other aspects, the devices 100, 200, 300, 400, 500 may include a combination of polymer components and metallic components. For example, the first and second bodies (e.g., 110, 120) may comprise a polymer, and the hinge pin 106, spring 138, and other fasteners for coupling the locking assembly to the first and second bodies, may include metals, such as stainless steel, aluminum, titanium, nickel, and/or any other suitable metal or alloy thereof.

The polymers used for the devices 100, 200, 300, 400, 500 may include polymers or plastics suitable for injection molding, 3D printing, vacuum casting, machining, or any other suitable manufacturing method. For example, one or more components of the devices described herein may include injection-molded acrylonitrile butadiene styrene (ABS), polycarbonate, nylon, polyethylene, polypropylene, polymethyl methacrylate, polyvinyl chloride, polyamide, polystyrene, thermoplastic elastomers (TPE), glass epoxy, acrylic, polyetheretherketone, polyarylamide, and/or any other suitable polymer. In some aspects, the polymer material(s) forming the components may be glass-filled or reinforced for increased strength.

Persons of ordinary skill in the art will appreciate that the implementations encompassed by the present disclosure are not limited to the particular exemplary implementations described above. In that regard, although illustrative implementations have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An apparatus for retaining spinal vertebrae in a distracted state, the apparatus comprising:
   a monolithic first body comprising:
      a first handle;
      a first jaw extending distally of the first handle; and
      a first canulated pin receiving member extending transverse to a longitudinal axis of the first body, wherein the first canulated pin receiving member comprises a tubular body extending from a distal end of the first handle,
      wherein at least one of the first handle or the first jaw comprises a first plurality of rib structures defining interstitial spaces;
   a monolithic second body pivotably coupled to the first body at an intermediate portion of the first body between the first handle and the first jaw, the second body comprising:
      a second handle;
      a second jaw extending distally of the second handle; and
      a second canulated pin receiving member extending transverse to a longitudinal axis of the second body, wherein the second canulated pin receiving member comprises a tubular body extending from a distal end of the second handle,
      wherein at least one of the second handle or the second jaw comprises a second plurality of rib structures defining interstitial spaces; and
   a locking assembly coupled to the first handle and the second handle, wherein the locking assembly is configured to selectively retain the first canulated pin receiving member and the second canulated pin receiving member at a plurality of relative spacings.

2. The apparatus of claim 1, wherein:
   the first jaw comprises an arcuate shape,
   the second jaw comprises an arcuate shape, and
   a distal end of the second jaw extends toward a distal end of the first jaw.

3. The apparatus of claim 1, wherein:
   the first body further comprises a first projection at the intermediate portion, wherein the first projection extends transverse to the longitudinal axis of the first body and defines a first hinge pin aperture,
   the second body further comprises a second projection at an intermediate portion of the second body, wherein the second projection extends transverse to the longitudinal axis of the second body and defines a second hinge pin aperture,
   the apparatus further comprises a hinge pin positioned through the first hinge pin aperture and the second hinge pin aperture to retain the first body and second body in a pivotable engagement.

4. The apparatus of claim 1, wherein the first canulated pin receiving member comprises a first flat surface on an inward-facing side of the first canulated pin receiving member, wherein the second canulated pin receiving member comprises a second flat surface on an inward-facing side of the second canulated pin receiving member, wherein the first flat surface is configured to contact the second flat surface when the apparatus is in a closed position.

5. The apparatus of claim 1, wherein the first body comprises a polymer material, and wherein the second body comprises the polymer material.

6. The apparatus of claim 1, wherein the first body further comprises at least one solid exterior surface over at least one side of the first plurality of rib structures, and wherein the second body further comprises at least one solid exterior surface over at least one side of the second plurality of rib structures.

7. The apparatus of claim 1, wherein the locking assembly comprises:
   a rack pivotably coupled to the first handle and the second handle, the rack comprising a first plurality of teeth;
   a pinion rotatably coupled to the first handle, the pinion comprising a second plurality of teeth configured to engage the first plurality of teeth; and
   a locking switch configured to lock the locking assembly at each of a plurality of positions corresponding to the plurality of relative spacings.

8. The apparatus of claim 7, wherein the first handle defines a first slot configured to receive a first end of the rack, and wherein the second handle defines a second slot configured to receive a second end of the rack.

9. The apparatus of claim 8, wherein the first end of the rack is configured to rotate within the first slot, and wherein the second end of the rack is configured to rotate within the second slot.

10. The apparatus of claim 7, wherein the rack further comprises a third set of teeth, wherein the locking switch further comprises a fourth set of teeth, wherein the locking assembly further comprises a spring configured to bias the locking switch to engage the fourth set of teeth with the third set of teeth.

11. The apparatus of claim 10, wherein the locking switch and the rack are configured to allow for ratcheting movement of the rack in a first direction and to inhibit movement of the rack in an opposite second direction.

12. The apparatus of claim 1, further comprising a first pin engaging member coupled to the first pin receiving member and a second pin engaging member coupled to the second pin receiving member, wherein the first pin engaging member comprises a first locking tab configured to engage a retaining groove on a first pin, and the second pin engaging member comprises a second locking tab configured to engage a retaining groove on a second pin.

13. The apparatus of claim 12, wherein the first pin engaging member is monolithic and comprises a flexible polymer, and wherein the second pin engaging member is monolithic and comprises a polymer.

14. The apparatus of claim 1, wherein the first jaw comprises a first transition region defining a curve projecting toward a pin-receiving end of the first canulated pin receiving member, and wherein the second jaw comprises a second transition region defining a curve projecting toward a pin-receiving end of the second canulated pin receiving member.

15. The apparatus of claim 1, wherein at least one of the first handle or the second handle comprises an I-beam structure.

16. The apparatus of claim 1, wherein the first plurality of rib structures interconnect and the second plurality of rib structures interconnect.

17. A vertebral retainer, comprising:
a monolithic first body comprising:
   a first handle;
   a first jaw extending distally of the first handle; and
   a first pin receiving member configured to retain a first pin;
a monolithic second body pivotably coupled to the first body at an intermediate portion of the first body between the first handle and the first jaw, the second body comprising:
   a second handle;
   a second jaw extending distally of the second handle; and
   a second pin receiving member configured to retain a second pin,
wherein the monolithic first body comprises a first plurality of rib structures in at least one of the first jaw or the first handle, the first plurality of rib structures defining a plurality of intersecting ribs and a plurality of voids, and
wherein the monolithic second body comprises a second plurality of rib structures in at least one of the second jaw or the second handle, the second plurality of rib structures defining a plurality of intersecting ribs and a plurality of voids.

18. The vertebral retainer of claim 17, wherein the first handle of the monolithic first body and the second handle of the monolithic second body are in a pivotable relative to each other about a pivot axis such that the first handle and the second handle are configured to apply a distracting force between a first vertebral body and a second vertebral body via the first pin and the second pin, respectively.

* * * * *